United States Patent [19]

Gewirtz

[11] Patent Number: 5,185,323

[45] Date of Patent: Feb. 9, 1993

[54] SUPPRESSION OF MEGAKARYOCYTOPOIESIS EMPLOYING PLATELET FACTOR 4 ANTIMATURATION FACTOR

[75] Inventor: Alan M. Gewirtz, Philadelphia, Pa.

[73] Assignee: Temple University, Philadelphia, Pa.

[21] Appl. No.: 175,552

[22] Filed: Mar. 31, 1988

[51] Int. Cl.[5] ............................................. C07K 15/06
[52] U.S. Cl. ........................................ 514/12; 514/21; 424/85.1
[58] Field of Search ..................... 514/12, 21; 530/380; 424/85.1

[56] References Cited

U.S. PATENT DOCUMENTS 4,702,908 10/1987 Thorbecke et al. ................... 424/88

OTHER PUBLICATIONS

A. Gewirtz, W. Y. Xu, B. Rueinski, and S. Niewiarowski, *Highly Purified Platelet Factor 4 Selectively Inhibits In Vitro Human Megacaryorytopoiesis*, Clinical Research, vol. 35, No. 3. Apr. 1987.

A. Gewirtz, B. Callabretta, B. Rucinski, and S. Niewiarowski, *Studies on the Mechanism of Platelet Factor 4 Induced Inhibition of Human Megacaryocytopoiesis in Vitro;* Blood, vol. 70 (Supplement #1), p. 153a, Nov. 1990.

Gewirtz et al. Jul. 6–10, 1987, Thromb. Haemostasis 58(1):493, Abstract No. 1822.

Primary Examiner—Robert A. Wax
Assistant Examiner—Keith C. Furman
Attorney, Agent, or Firm—Ratner & Prestia

[57] ABSTRACT

Antimaturation factor (platelet factor 4 or active peptide segments thereof) is employed in the clinical treatment of coagulation disorders as an anticoagulant operating via an autoregulator mechanism for selectively suppressing megakaryocytopoiesis. Exposure of immature megakaryocytes to antimaturation factor reversibly inhibits cell maturation and, accordingly, functions characteristic of the mature cell, including platelet production and expression of genes coding for platelet coagulation factors, are reversibly suppressed.

27 Claims, 3 Drawing Sheets

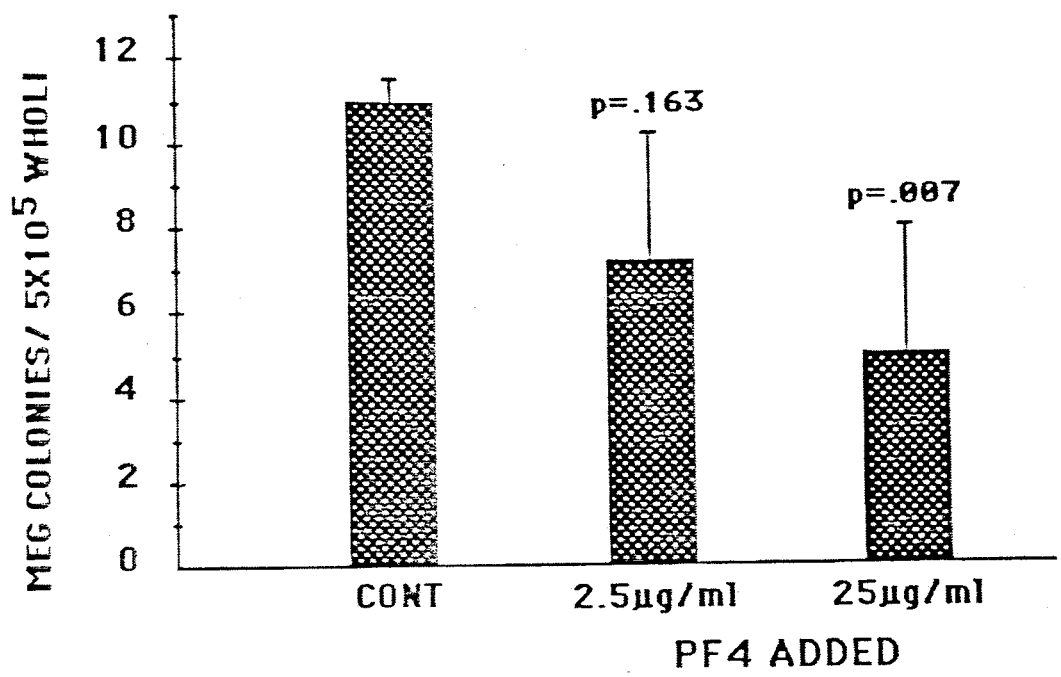
FIG. 1
FIG. 2A FIG. 2B FIG. 2C
FIG. 2D FIG. 2E FIG. 2F

SUPPRESSION OF MEGAKARYOCYTOPOIESIS EMPLOYING PLATELET FACTOR 4 ANTIMATURATION FACTOR

BACKGROUND OF THE INVENTION

Pluripotent hematopoietic stem cells are activated in the bone marrow to proliferate and differentiate into mature megakaryocytes, each of which is capable of releasing up to several thousand functional platelets in response to biological demand. Development of the stem cell proceeds by stages broadly corresponding to proliferation of progenitor cells, and differentiation of late progenitor and early precursor cells into mature megakaryocytes. Although regulation of this developmental process (megakaryocytopoiesis) is of substantial clinical interest for its potential application to disorders characterized by abnormal platelet production, endogenous factors responsible for stimulating or inhibiting proliferation and differentiation of megakaryocyte progenitor/precursor cells have not been thoroughly elaborated.

In particular, inhibition factors capable of clinically significant megakaryocyte suppression have not been well-characterized. For example, both immunocytes and transforming growth factor-$\beta$(TGF-$\beta$) have been studied as potential inhibitors of megakaryocytopoiesis, with inconclusive results (see, e.g., Blood 67: 479-483 and 68: 619-626, 1986). Additionally, autoregulation via negative feedback mechanisms involving megakaryocyte products, including plateletsecreted 12-17kD glycoprotein, has been reported (J. Cell Physiol. 130: 361-368, 1987). While the potential utility of negative autocrine regulators or other megakaryocytopoiesis inhibitors in the clinical treatment of disorders characterized by excessively high platelet counts is apparent, none of the heretofore postulated inhibitors has so far proved useful in such applications.

BRIEF DESCRIPTION OF THE DRAWINGS

FIG. 1 graphically illustrates the effect of highly purified platelet factor 4 (PF4) on clonogenicity of normal human megakaryocyte progenitor cells in plasma clot culture. Bone marrow mononuclear cells (MNC) were isolated by density gradient sedimentation and then suspended in the appropriate culture medium, to which was added PF4 in the amounts indicated. The cell suspensions were plated, and cultured for twelve days at 37° C. in a humidified environment containing 5% $CO_2$, and resulting megakaryocyte colonies were then enumerated in situ with an indirect immunofluorescence assay using a polyspecific antiplatelet glycoprotein antiserum as probe. Aggregate results (mean±S.D.) of five separate experiments are shown. Numbers at top of bars indicate p value in comparison to control (CONT.).

FIG. 4 graphically illustrates the effect of highly purified platelet factor 4 (PF4) on clonogenicity of normal human erythroid colony forming units (CFU-E) in plasma clot culture in the absence of accessory marrow immunocytes. Isolated bone marrow mononuclear cells (MNC) were depleted of adherent monocyte-macrophages and lymphocytes, as detailed in the Examples. After seven days in culture, plates were harvested and fixed and CFU-E detected by benzidine staining. Results of three separate experiments, each performed in quadruplicate culture plates, are shown.

BRIEF DESCRIPTION OF THE INVENTION

Figure 2:
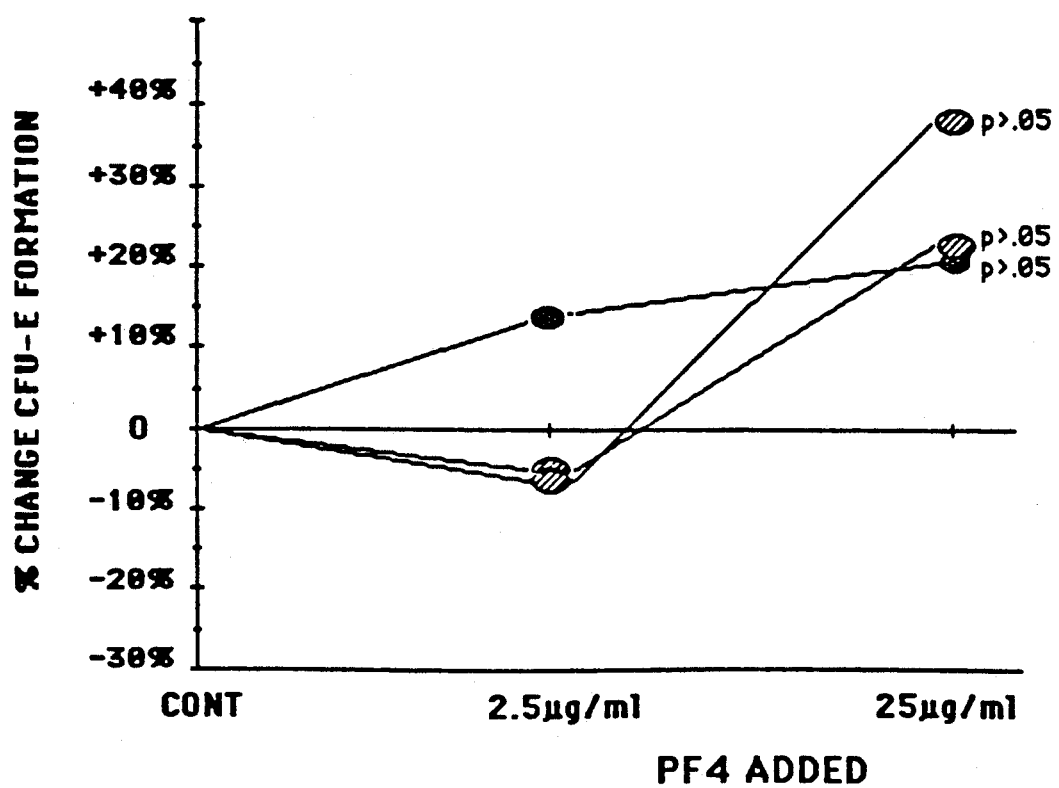
FIG. 2 is a composite photomicrograph of normal human megakaryocytes probed for expression of $\beta$-actin and coagulation cofactor V (FV) mRNA by in situ hybridization with DNA probes labeled by random priming with biotin-11-dUTP, illustrating the effect of PF4 on expression of FV mRNA in human megakaryocytes. Megakaryocytes were separated from normal human bone marrow by counterflow centrifugal elutriation, and then placed in suspension cultures for sixteen to eighteen hours in medium containing either a synthetic "long" PF4 peptide (100 $\mu$g/ml) or no PF4. DNA-RNA hybridizations are indicated by the appearance of purple-brown precipitate over the cytoplasm of the cell; the greater the amount of hybridization that occurs, the darker and denser the precipitate that forms. Appearance of cells post-hybridization with probes for pBR322 and 8-actin is shown in Panels A and B, respectively. Panel C demonstrates the appearance of cells pre-treated with RNase A (500 $\mu$g/ml) for ~on hour prior to hydridization with 8-actin probe. Panels D and E illustrate representative color development for megakaryocytes hybridized with FV probe (note arrows) two small, unlabeled mononuclear cells on Panel D megakaryocyte). Panel F shows representative color occurring in megakaryocytes hybridized with FV probe after sixteen to eighteen hour incubation in PF4.

According to the invention, platelet factor 4 (PF4), a megakaryocyte/platelet-specific $\alpha$-granule protein, has been identified as a negative autocrine regulator with clinical utility in the treatment of coagulation disorders characterized by excessively high platelet counts. Both PF4 and active PF4 peptide segments suppress megakaryocyte maturation (differentiation) without significant inhibitory effect on progenitor/precursor cell proliferation, and are characterized herein as selective megakaryocyte Antinaturation factors which inhibit development of immature late progenitor/early precursor cells into platelet-producing mature megakaryocytes.

It has additionally been found that PF4 and active peptide segments thereof (herein generically referred to as Antimaturation factor) inhibit the expression of genes coding for platelet coagulation factors in megakaryocytes. Exposure of immature megakaryocytes to Antimaturation factor thus results in mature cells which produce platelets deficient in these coagulation factors and which cannot, therefore, fully participate in the normal coagulation "cascade."

Antimaturation factor accordingly comprises an anticoagulant potentially useful in the treatment of a variety of coagulation disorders associated with platelet/platelet coagulation factor overabundance. Since PF4 Antimaturation factor is synthesized by platelets, and suppresses megakaryocyte maturation in a reversible and saturable manner, PF4 Antimaturation factor is a bona fide negative autoregulator of megakaryocytopoiesis and, accordingly, safe, effective clinical use is contemplated.

DETAILED DESCRIPTION OF THE INVENTION

According to the invention, PF4 and active peptide segments thereof are employed to inhibit megakaryocytopoiesis to effect reduction of platelet production in vivo, as measured by blood platelet count, and to inhibit production of platelet coagulation factors. Sufficient PF4 or active peptide segment is employed to effect the desired reduction in platelet count, preferably by intravenous administration. Depending upon the route of administration and idiosyncratic factors, particularly individual platelet counts and rates of Antimaturation factor clearance, average dosages of up to about 12 gms active material per day in humans are contemplated.

Both PF4 and active peptide segments thereof are useful in the process of the invention as PF4 anti-maturation factor. PF4 is a known α-granule protein specific to platelets, which exists in the unactivated platelet as a granulated tetramer composed of identical 7800 kD monomers, as more fully described in *The Platelet's Physiology and Pharmacology*, Niewiarowski, et al. (Academic Press Inc. N.Y. 1985), especially pp. 49-83 thereof; *Proc. Nat'l Acad. Sci.* USA 74: 2256-2258 (1977); *J. Biol. Chem.* 252: 6276-6279 (1977); and *Biochim. Biophys. Acta* 286: 312-329 (1972) PF4 is readily obtained by purification from human platelets according to published procedures (see, e.g., *Blood* 53: 47-62, 1979). As used herein, the term Antimaturation factor includes active PF4 peptide segments having amino acid sequences corresponding or homologous to amino acid sequences of the PF4 protein molecule, referred to as "PF4 corresponding peptide segments" and "PF4 homologous peptide segments," respectively. The term "active PF4 peptide segments" accordingly generically includes PF4 corresponding peptide segments and PF4 homologous peptide segments, wherein one or more amino acids in a PF4 corresponding peptide segment are substituted with a different amino acid, with the proviso that the PF4 peptide segment functions to suppress megakaryocytopoiesis and/or inhibit megakaryocyte maturation; i.e., is "active" within the scope of the invention. The segments may be derived from naturally-occurring proteins, or be synthesized according to well-established procedures. Since it is believed that the inhibitory activity of PF4 peptide segments may be localizable to the carboxy-terminal domains thereof, such c-terminal segments are presently preferred. Generally, greater activity tends to be found in segments containing at least about 24 carboxy-terminal amino acid residues (e.g., at least residues #46-70 of PF4), and the use of such segments is accordingly recommended.

Antimaturation factor according to the invention is contemplated for use in lowering blood levels of circulating platelets as deemed clinically advantageous, and for use in reducing the ability of these platelets to support blood clot formation. As described in the Examples herein, in addition to suppressing megakaryocyte platelet production, a function of the mature cell, PF4 Antimaturation factor additionally suppresses megakaryocyte expression of mRNA coding for platelet procoagulation factors, especially platelet coagulation cofactor V (FV). Since production of cofactor V is also a characteristic of mature megakaryocytes, platelet deficiency in this cofactor, after exposure of the parent megakaryocyte to PF4 Antimaturation factor, both evidences the antidifferentiation function of PF4 and reinforces the anticoagulant activity thereof.

Pathological vascular reactions associated with excessively high platelet counts include stroke, pulmonary emboli, and related thromboembolic complications. A predisposing factor for these potentially fatal complications, high circulating platelet levels, can be substantially minimized by administration of Antimaturation factor according to the invention. Since PF4 Antimaturation factor also inhibits production of coagulation cofactor V, the therapeutic use of this PF4 factor also stimulates the production of platelets less able to support blood clot formation, and is therefore broadly indicated in the treatment of diseases or disorders with a prominent thromboembolic risk, whether or not accompanied by high platelet counts. The invention is of particular clinical relevance in the treatment of myeloproliferative and other disorders characterized by clinically disadvantageous high platelet counts, as well as coagulation disorders more broadly characterized by a high thromboembolic component with attendant risk of heart attack, venous thrombosis, stroke, pulmonary emboli, or related vascular accidents.

Treatment of such diseases or disorders is accomplished according to the process of the invention by the administration of PF4 or active peptide segments thereof in sufficient quantities to suppress platelet production and approach normal hemostasis, as measured by significant reduction in blood platelet count. Generally, a clinically significant effect comprises a reduction in platelet count of at least about 10%. Contemplated routes of administration include intravenous and parenteral routes, including per os. Therapeutic dosages of up to about 12 grams Antimaturation factor per day per 150 lbs. body weight comprise a general guideline for effecting the desired platelet count reduction or change in procoagulant activity.

In view of the previously described immunomodulatory activity of PF4 (see, e.g., *J. Immunol.* 134; 3199-3203, 1985), the efficacy of the process of the present invention is unexpected. In particular, it has been reported that platelet α-granule releasates augment immune response in mice (*J. Immunol., ibid.*) and further, that CD4+"helper" T lymphocytes promote megakaryocytopoiesis (see, e.g., *J. Immunol.* 137: 2508-2513, 1986; *Blood* 68: 991-995, 1986). Accordingly, PF4 augmentation of megakaryocytopoiesis would be expected. To the contrary, as described herein, PF4 suppresses megakaryocytopoiesis. Moreover, in contrast to prior art inhibitors such as TGF-β, which suppress hematopoiesis in a more general response, Antimaturation factor specifically inhibits megakaryocytopoiesis in a reversible, saturable manner. As a selective endogenous auto-regulator of megakaryocytopoiesis, PF4 Antimaturation factor not utilized in megakaryocyte suppression is readily cleared from the blood. Further, the reversibility of the reaction ensures that dosages can be optimized on a trial-and-error basis without risk of irreversible side-effects, and the selectivity of the factor minimizes potential involvement of related pathways. Accordingly, PF4 Antimaturation factor is contemplated for use as a safe, efficacious therapeutic for suppression of platelet production and platelet coagulation factor determinants by megakaryocyte target cells.

EXAMPLES

Methods and Materials

A. Preparation of Antimaturation Factor

Purification of PF4 and Synthesis of Synthetic C-terminal PF4 Active Peptide Segments Human PF4 was ified essentially as published (*Blood* 53: 47-62, 1979). In brief, outdated human platelets were thrombin-stimulated. The resulting supernatant was applied to a heparin-agarose column. The column was washed, and the PF4 specifically eluted with 1.5M NaCl. Some PF4 preparations were purified from the supernatants of stored, outdated platelets by a combination of Sephadex G-75 gel filtration, and heparin a9arose column chromato9raphy. Eluted fractions were pooled, and then stored lyophilized. Such preparations gave a sin9le band on SDS-Polyacrylamide gels, and were judged to >95% pure.

Synthetic PF4 peptides were commercially synthesized and purified (Pennisula Laboratories, Belmont, CA). Purity and sequence were confirmed by the Macromolecular Analysis and Synthesis Laboratory, Temple University School of Medicine, by Edman Degradation using Applied Biosciences instrumentation. The peptides utilized consisted of either the terminal 13 (amino acid residues #58-70), or terminal 24 amino acids (residues #46-70) in the 70 amino acid human PF4 sequence. These were designated "short" and "long" PF4 peptide, respectively.

B. Cells and Tissue Culture Methods

Megakaryocyte Cell Assay

Megakaryocyte colonies were cloned in plasma clot cultures as previously described (e.g., *Blood* 61: 384-9, 1983). The cell population cultured consisted of either unseparated high density marrow mononuclear cells (MNC), or MNC depleted of adherent monocytemacrophages (MO) and T lymphocytes using methods previously reported (e.g., *J. Immunol.* 2915-2925, 1987). To provide essential growth factors, all cultures were supplemented with normal human AB serum (30% v/v) derived from the platelet-poor plasma of a single donor.

Megakaryocyte colonies were enumerated by indirect immunofluorescence assay utilizing a rabbit anti-human platelet glycoprotein antiserum as a megakaryocyte probe (*ibid.*). The antiserum utilized is highly specific for recognition of platelet glycoproteins, and it does not recognize monocytes. A cluster of three or more intensely fluorescent cells was counted as one colony. Unless otherwise stated, all data are reported as the mean± S.D. of colonies enumerated.

Isolation of Mature Marrow Megakaryocytes

Mature (morphologically recognizable) megakaryocytes were isolated from the marrow of normal bone marrow donors by the process of counterflow centrifugal elutriation (CCE), as previously described (e.g., *Blood* 37: 1639-1648, 1986). Such cells were then utilized for culture, or suspended in Supplemented Alpha medium containing 5% normal human AB serum (derived from the platelet poor plasma of a single donor) and subjected to short-term culture, either in the presence or absence of 100 μg/ml of synthetic "long" C-terminal PF4 peptide (see below). After culture, cells were fixed in 4% paraformaldehyde, and stored in 70% ethanol at 4° C. for use in situ hybridizations (see below).

C. Molecular Analysis Methods

Isolation of RNA

Total cellular RNA was purified from cells as previously described (ibid.) In brief, cells were homogenized in a Waring blender in nucleic acid extraction buffer (75mM NaCl, 20mM EDTA, 10mM Tris-HCL, ph 8.0, and 0.2% sodium dodecyl sulfate), mixed 1:1 with buffer-saturated phenol. The aqueous phase was recovered by centrifugation, re-extracted with an equal volume of phenol and chloroform:isoamyl alcohol (25:24:1), and finally with chloroform:isoamyl alcohol (24:1). Nucleic acids were precipitated with two-and-one-half volumes of ethanol, and DNA removed by treatment with DNase 1 and precipitation with 3M sodium acetate (pH 5.5). The integrity and amount of RNA samples were monitored by ethidium bromide staining of agarose-formaldehyde gels.

In situ Hybridization Procedure

In situ hybridization was performed using a synthesis of the techniques described in *Virology* 126: 32-50, 1983 and *Biotechniques* 4: 39-39 230-250, 1986. Human megakaryocytes, fixed and stored as described above, were deposited onto glass slides by cytocentrifugation (500 rpm × 8 minutes, Cytocentrifuge II, Shandon Southern, Sewicky, PA). Prehybridization washes, including treatment with acetic anhydride (0.1% in triethanolamine), were carried out as described (*ibid.*). Hybridization was carried out using DNA probes oligolabeled with biotin-11-dUTP (BRL, Gaithersburg, MD) using the method of *Ann. Biochem.* 137: 266-267, op. cit. 25 μl of probe [(100ng/ml of hybridization cocktail containing 45% formamide (Amersco, Solon, Ohio)] was layered over the specimen which was then covered with a glass slide, sealed in parafilm, and then hybridized for ~18 hours at 37° C. Post-hybridization washes were carried out as described in *Biotechniques* 4: 32-39, op. cit., the final wash being carried out in 0.16% SSC at room temperature. DNA-RNA hybrids were detected with a DNA Detection Kit, essentially as described by the manufacturer (BRL, Gaithersburg, MD). Positive reactions consisted of a purple to deep brown colored precipitate in the cell's cytoplasm. The degree of hybridization correlates directly with the amount of precipitate accumulated in the cell.

Hybridization with pBR322 was carried out as a negative control. An additional control consisted of pre-treating specimens with RNase A (500 μg/ml) prior to hybridization with the probe of interest. Hybridization with a cDNA coding for human β-Actin was employed as a positive control.

Reactions were semi-quantitated by computer assisted microspectrophotometry (Zonax, Carl Zeiss, Mineola, N.Y.) as a function of light transmission through the object cell. The photometer was standardized so that light transmission through a clear area of the slide containing no cells (background) was defined as 100% transmission, while no light falling on the photometer was defined as 0% transmission. Identical gain and high voltage setting were employed throughout.

D. Plasmids

Plasmids containing the cDNA inserts used as probes in these experiments have been previously described pUC9 carrying the human coagulation factor V (FV) gene probe was provided by University of Washington, Seattle, Washington. pBR322 was obtained from the American Type Culture Collection (Rockville, MD). The Department of Pathology, Temple University Medical School, supplied plasmids containing human β-actin inserts.

E. Statistical Analysis

Statistical significance of differences between groups was tested using a two-tailed Student's T Test for unpaired observations.

EXAMPLE I. Characterization of PF4 and active PF4 peptide segments as Antimaturation factor I.A. Effecto of PF4 on megakaryocyte colony formation (proliferation assay).

To determine if PF4 could modify megakaryocyte colony formation in vitro, a screen assay was performed by adding various amounts of pure protein to unseparated marrow MNC. To emulate basal growth conditions in marrow, the cultures contained no exogenous source of growth factors, and were supplemented only with normal human AB serum derived from platelet-poor plasma The aggregate results of five such experiments are shown in FIG. 1. In the control condition, ~11 colonies per $2\times10^5$ MNC plated were enumerated. In the presence of 2.5 µg/ml of PF4, ~7 colonies were counted. This difference was not significant (p>0.05). However, in the presence of 25 µg/ml of PF4, a mean of five colonies was enumerated and this difference was highly significant (p<0.007).

I.B Effect of synthetic c-terminal PF4 peptides on megakaryocyte colony formation (proliferation assay).

These preparations were employed to exclude from consideration that the inhibitory effect observed in Example IA might be due to impurities in the PF4 preparation, and to determine whether the colony inhibitory effect observed might be localizable to the c-terminal domain of PF4. Also, since secondary and tertiary structure are important in mediating a protein's biological activities, it was of interest to obtain structure/function information by employing these peptides in the described bioassay system. One peptide consisted of the last 13 amino acid residues from the carboxy terminus and was designated "short peptide." The other consisted of the last 24 residues and was designated "long" peptide.

The results of four experiments with the synthetic c-terminal peptides are shown in Table 1. As indicated, the short and long peptides were tested in a dose response manner at 2.5, 25 and 50 µg/ml concentrations. The short peptide demonstrated inhibitory activity in only one of the three studies performed, and this was at the highest concentration tested. In contrast, inhibitory activity was more consistently noted with the long peptide.

In two of three experiments, long peptide inhibited colony formation at 25 µg/ml concentration, and in four experiments at the 50 µg/ml concentration. These results indicate that results with the purified PF4 protein were not due to artifact and that the carboxyterminal domain of the protein contains at least part of the inhibitory activity noted in the above experiments.

I.C. Effect of PF4 carboxy-terminal segment on megakaryocyte maturation and progenitor cell proliferation.

First, to assess potential effects on progenitor cell proliferation, the total numbers of cells comprising each individual colony in two hundred control colonies and in one hundred colonies cloned in plates containing "long" PF4 peptide were enumerated. Control colonies were found to contain 6.1±3.0 (mean ±S.D) cells per colony, while colonies grown in the PF4 containing plates contained 4.2+1.6 cells per colony. This difference was small, but of statistical significance (p<0.001) (Table 2). The number of "large" (mature) cells and "small" (immature) cells in these same colonies were then quantitated as an index of effect on cell maturation (Table 2). Control colonies were composed of 3.9±2.3 large cells, while those arising in PF4 containing plates had 1.6±1.6 large cells. This 59% reduction in large cells was highly significant (p<0.001). In contrast, there were 2.1±2.1 small cells in control colonies in comparison to 2.6±1.8 in plates containing PF4. In aggregate, these results demonstrate that PF4 exerts a greater effect on megakaryocyte maturation than on megakaryocyte progenitor cell proliferation.

TABLE 2

Effect of Long Synthetic C-terminal PF4 Peptide on Megakaryocyte Maturation and Progenitor Cell Proliferation Marrow mononuclear cells were prepared and cultured as described in the legends for Tables 1 and 3 and in "Methods and Materials." Long PF4 was added at a final concentration of 50 µg/ml. Colonies were identified by indirect immunofluorescence and analyzed in situ at total magnifications of 100X and 400X.

|  | Control Colonies (n = 200) | Colonies Cloned in PF4 (n = 100) |
|---|---|---|
| Total Cells/Colony | 6.1 ± 3.0+ | 4.2 ± 1.6* |
| "Large" Cells/Colony | 3.9 ± 2.3 | 1.6 ± 1.6* |

TABLE 1

Effect of Synthetic C-terminal PF4 Peptides on Megakaryocyte Colony Formation

Light density marrow mononuclear cells were depleted of adherent monocyte-macrophages and T lymphocytes, and then cloned in plasma clot cultures as described in the Experimental Procedures section. "Short" (13 AA residues) and "Long" (24 AA residues) synthetic PF4 peptides were then added to the cultures in dose response fashion and resulting megakaryocyte colonies enumerated as described.

| STUDY # | Control (C) Cells | SHORT PEPTIDE | | | LONG PEPTIDE | | |
|---|---|---|---|---|---|---|---|
|  |  | 2.5 µg/ml | 25 µg/ml | 50 µg/ml | 2.5 µg/ml | 25 µg/ml | 50 µg/ml |
| 1 | 31 ± 1 | 31 ± 5 | 33 ± 2 | 28 ± 4 | 37 ± 5 | 23 ± 2 (p = .05)+ | 9 ± 6 (p = .05) |
| 2 | 113 ± 12 | 157 ± 12 | 107 ± 10 | 94 ± 8 | 88 ± 14 | 144 ± 17 | 50 ± 26 (p = .05) |
| 3 | 7 ± 1 | 5 ± 0 | NT* | 1 ± 0 (p = .01) | 8 ± 2 | NT | 1 ± 1 (p = .01) |
| 4 | 24 ± 5 | NT | NT | NT | 18 ± 4 | 10 ± 2 (p = .03) | 10 ± 1 (p = .02) |

Mean ± SEM of megakaryocyte colonies enumerated in quadruplicate culture plates
+ p statistic in comparison to growth in control plates
*NT = not tested TABLE 2-continued Effect of Long Synthetic C-terminal PF4 Peptide on Megakaryocyte Maturation and Progenitor Cell Proliferation Marrow mononuclear cells were prepared and cultured as described in the legends for Tables 1 and 3 and in "Methods and Materials." Long PF4 was added at a final concentration of 50 μg/ml. Colonies were identified by indirect immunofluorescence and analyzed in situ at total magnifications of 100X and 400X.

|  | Control Colonies (n = 200) | Colonies Cloned in PF4 (n = 100) |
|---|---|---|
| "Small" Cells/Colony | 2.1 ± 2.1 | 2.6 ± 1.8 | n = total number of colonies examined
+Mean ± SD of total cells enumerated
*p < .0001

I.D. Effect of PF4 and a carboxy-terminal active peptide segment thereof on megakaryocyte maturation employing FV as marker (maturation assay).

Coagulation cofactor V (FV) was chosen as a suitable marker since this protein is expressed only in more mature cells of the megakaryocyte lineage. Normal, mature human megakaryocytes were isolated from bone marrow by centrifugal elutriation, and suspended for up to twenty-four hours in liquid cultures containing 100 μg/ml of synthetic "long" PF4 peptide. The cells were then fixed as described above and probed for the expression of FV mRNA by the technique of in situ hybridization using a biotinylated cDNA probe. Results of typical experiment are shown in a composite photomicrograph (FIG. 2, Panels A-F). Cells in Panel A were hybridized with a pBR322 probe and are unlabeled. In Panel B, cells were probed with an insert for human β-actin and are strongly labeled. This signal is essentially eliminated by pre-treating cells with RNase (500 μg/ml) prior to hybridization as shown in Panel C Panels D-E show typical signal achieved after hybridization with the FV cDNA probe. Panel F demonstrates the marked reduction in signal noted after incubation of PF4 for 16-18 hours. Dose response testing revealed comparable decreases in FV mRNA expression at concentrations of long peptide to 100 ng/ml. At 20 ng/ml, the effect was no longer detectable.

Accumulation of indicator dye was semiquantititated by microspectrophotometry as described under "Materials and Methods." Since increasing amount of hybridization correlates directly with the density of dye accumulation in a given cell, and increasing dye accumulation impedes light transmission through any given cell being examined, those cells which allow the greatest degree of light transmission are expressing the least amount of message. It is emphasized that, since the photometer is not as sensitive to grey scale changes within a color family as it is to black and white, differences recorded are underestimates of true changes observed (FIG. 2).

Light transmission through mononuclear cells was found to be quite constant after hybridization with the FV probe, regardless of the conditions under which the cells were cultured. MNC in the control suspension cultures (number examined [n]=228) were found to allow 73.2±7.5% light transmission (100% maximum), while similar cells exposed to 100 μg/ml of synthetic PF4 peptide permitted 72.8+7.8% light transmission ([n]=216). These differences were of no statistical significance (p=0.559). In contrast, light transmission through megakaryocytes incubated in PF4 was 64.4±8.4% post-hybridization ([n]=292) with the FV cDNA probe, versus 58±9.5% in the control cells ([n]=298). This difference, while small in absolute terms, was highly significant (p<.001). If the change in light transmission in these groups is compared to that permitted by the "unlabeled" MNC, it is calculated that control megakaryocytes had 60% greater dye accumulation than cells incubated in PF4 [73%–68%=Δ9; 73%–58%=Δ15; 9/15=.6]. Since these differences are underestimates of true change in color, these data are indicative of a highly significant decline in FV mRNA, post-exposure to PF4.

EXAMPLE II. Characterization of Antimaturation factor activity as non-T lymphocyte dependent: effect of T cells and T cells plus PF4 on megakaryocyte colony formation.

Since the majority of marrow T lymphocytes are of the suppressor type, and PF4 is described in the prior art as inactivating these cells, the results obtained in Examples IA and IB were unexpected. In fact, it was anticipated that colony formation might be increased because of unopposed T helper activity. Putative progenitor cell-T cell-PF4 interactions were accordingly studied. Control target cells, depleted of adherent monocytes and T lymphocytes were cloned in plasma clots under standard conditions (Table 3). Aliquots of these target cells were also cloned in the presence of either CD4+helper, or CD8+suppressor T cells alone, or T effector cells plus PF4 at two different concentrations, 2.5 and 25 μg/ml.

TABLE 3

Effect of Co-Culturing Human Megakaryocyte Progenitor Cells and T Lymphocyte Subsets in the Presence of Different Amounts of Highly Purified PF4

Light density marrow mononuclear cells were depleted of adherent monocyte-macrophages, and T lymphocytes. They were then cloned in plasma clots (2 × 10⁵/ml) with autologous T lymphocyte subsets, in the presence of varying amounts of purified PF4 as described in Experimental Procedures. Megakaryocyte colonies were enumerated in situ by indirect immunofluorescence.

| STUDY # | Control (C) Cells | C/T4 2:1§ | C/T4 2:1 + PF4 2.5 μg/ml | C/T4 2:1 + PF4 25 μg/ml | C/T8 2:1 | C/T8 2:1 + PF4 2.5 μg/ml | C/T8 2:1 + PF4 25 μg/ml |
|---|---|---|---|---|---|---|---|
| 1 | 7 ± 2+ | 11 ± 0 | 8 ± 1 | NT# | 6 ± 1 | 18 ± 2 | NT |
| 2 | 4 ± 1 | 3 ± 1 | 5 ± 1 | NT | NT | NT | NT |
| 3 | 11 ± 3 | 10 ± 0 | NT | NT | NT | 7 ± 2 | 1 ± 0* |
| 4 | 116 ± 6 | 141 ± 22 | 122 ± 29 | 8 ± 1* | 163 ± 13 | 87 ± 15* | 13 ± 2* |

TABLE 3-continued

Effect of Co-Culturing Human Megakaryocyte Progenitor Cells and T Lymphocyte Subsets in the Presence of Different Amounts of Highly Purified PF4

Light density marrow mononuclear cells were depleted of adherent monocyte-macrophages, and T lymphocytes. They were then cloned in plasma clots ($2 \times 10^5$/ml) with autologous T lymphocyte subsets, in the presence of varying amounts of purified PF4 as described in Experimental Procedures. Megakaryocyte colonies were enumerated in situ by indirect immunofluorescence.

| STUDY # | Control (C) Cells | C/T4 2:1§ | C/T4 2:1 + PF4 2.5 µg/ml | C/T4 2:1 + PF4 25 µg/ml | C/T8 2:1 | C/T8 2:1 + PF4 2.5 µg/ml | C/T8 2:1 + PF4 25 µg/ml |
|---|---|---|---|---|---|---|---|
| 5 | 33 ± 6 | 39 ± 4 | NT | 3 ± 1* | NT | 33 ± 4 | 3 ± 1* |

Monocyte-macrophage, and lymphocyte depleted marrow mononuclear cells - $2 \times 10^5$/ml
§ Ratio of Control cells to T lymphocytes
+Mean ± SEM of colonies enumerated in quadruplicate culture plates
NT = not tested
*p < .05

In agreement with previous results from our laboratory *J. Immunol.* 139: 2915-2924, 1987], adding nonactivated CD4+(helper) cells had inconstant effects on megakaryocyte colony formation. These results were unchanged by the addition of PF4 at concentration of 2.5 µg/ml. However, consistent with the results obtained in EXAMPLE I (FIG. 1), the addition of high concentration of PF4 resulted in a highly significant decrease in colony formation.

These results show the colony suppressive effect of PF4 was indifferent to the presence of T lymphocytes, implying that PF4 has a direct suppressive effect on colony formation.

Figure 3:
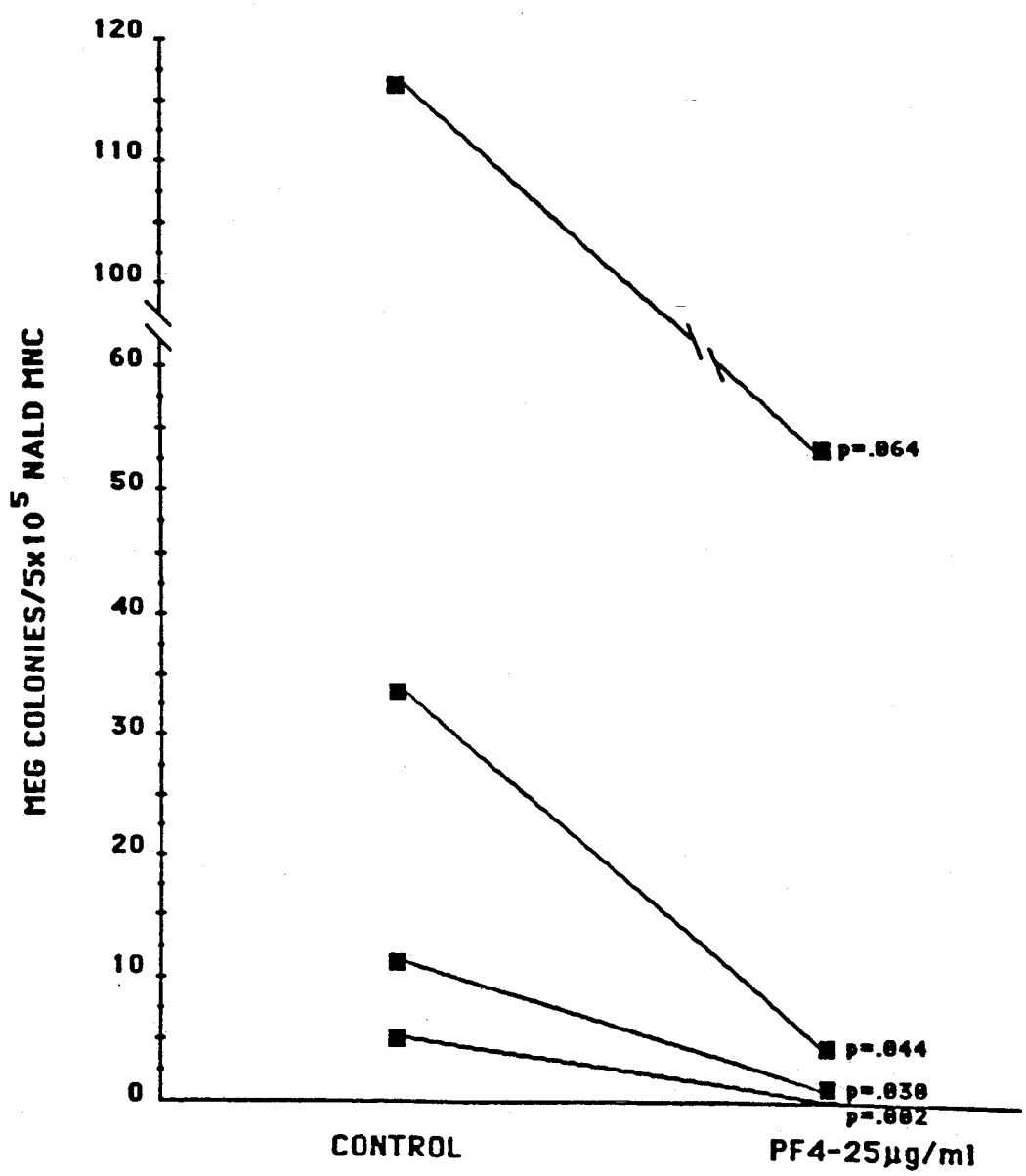
FIG. 3 graphically illustrates the effect of highly purified platelet factor 4 (PF4) on normal human megakaryocyte colony formation in vitro in the absence of accessory marrow immunocytes. Isolated bone marrow mononuclear cells (MNC) were depleted of adherent monocyte-macrophages and lymphocytes and treated as detailed in the Examples. Each line represents the result of a single experiment performed in quadruplicate culture plates. p values in comparison to control are indicated for each experiment.

To determine if PF4 had a direct suppressive effect on the growth/maturation of megakaryocyte progenitor/precursor cells, purified material was added to culture plates containing marrow mononuclear cells depleted of adherent monocytes and T lymphocytes. The results of four experiments of this type are shown in FIG. 3. As indicated, at the 25 µg/ml concentration colony formation was greatly inhibited in each of the experiments. The mean inhibition was ~78%.

EXAMPLE III. Characterization of PF4 and active carboxy-terminal segment as megakaryocyte-specific: effect of PF4 on erythroid colony formation (specificity assay).

The effect of purified protein on inhibition of erythroid colony formation was tested. As shown in FIG. 4, no inhibition of erythroid colony formation units (CFU-E) was noted at concentrations of PF4 which consistently inhibited megakaryocyte colony formation. These results indicate that the effect of PF4 is lineage specific.

EXAMPLE IV. Exemplary Clinical Protocol

Contemplated guidelines for the clinical use of Antimaturation factor are as follows:

5 gm Antimaturation factor is administered intravenously or by mouth in the form of PF4 purified as described under "Methods and Materials," *supra.*, to a 150 lb. male patient having distal ischemia, stroke, or other thromboembolic phenomena attributed to abnormal platelet count or function. The platelet count and platelet function are monitored from seven to ten days after administration by analysis of blood samples taken at four-hour intervals to evaluate PF4 potency (which may vary with the donor) and blood clearance rate. At the end of the evaluation period, the dosage is adjusted as necessary to establish an improved platelet count or function, and the patient is again monitored once or twice weekly, as described. At the end of this period, PF4 dosage is again adjusted as necessary, with repetition of the described monitoring and evaluation procedures until the platelet count is substantially stabilized at a normal or near-normal level or the procoagulant function of the platelet is lessened to the desired degree. The dosage required to obtain the desired stabilized platelet count comprises a therapeutic dosage according to the invention.

Owing to a short half-life (measurable in minutes in rodents) of Antimaturation factor in the bloodstream, administration of the therapeutic dosage on a daily basis to maintain platelet levels may be necessary.

I claim:

1. A method for reducing the number of circulating platelets in the bloodstream of a mammal, comprising administering to the mammal a sufficient amount of Antimaturation factor to effect said reduction.

2. The method of claim 1, wherein the Antimaturation factor is intact platelet factor 4.

3. The method of claim 1, wherein the Antimaturation factor is an active peptide segment of platelet factor 4.

4. The method of claim 3, wherein the active peptide segment is a carboxy-terminal segment.

5. The method of claim 4, wherein the active peptide segment contains at least about 24 amino acid residues.

6. The method of claim 1, wherein an amount of Antimaturation factor is administered sufficient to reduce the number of circulating platelets by at least about 10%.

7. A method for stimulating in a mammal the production of platelets deficient in at least one platelet coagulation factor, comprising administering to the mammal a sufficient amount of PF4 Antimaturation factor to effect said deficiency.

8. The method of claim 7, wherein the Antimaturation factor is platelet factor 4.

9. The method of claim 7, wherein the Antimaturation factor is an active peptide segment of platelet factor 4.

10. The method of claim 9, wherein the active peptide segment is a carboxy-terminal segment.

11. The method of claim 10, wherein the active peptide segment contains at least about 24 amino acid residues.

12. The method of claim 7, wherein the coagulation factor is cofactor V.

13. The method of claim 12, wherein the Antimaturation factor is platelet factor 4.

14. The method of claim 12, wherein the Antimaturation factor is an active peptide segment of platelet factor 4.

15. The method of claim 1, wherein at least some of the circulating platelets after said administration are deficient in at least one platelet coagulation factor.

16. The method of claim 15, wherein the deficient factor is platelet coagulation cofactor V.

17. The method of claim 16, wherein the Antimaturation factor is platelet factor 4.

18. A method for the clinical treatment of a thromboembolic disease or disorder, comprising administering to a human affected with said disease or disorder an anticoagulant comprising Antimaturation factor in an amount sufficient to reduce the thromboembolic component of said disease or disorder.

19. The method of claim 18, wherein the Antimaturation factor is administered in an amount sufficient to reduce the number of platelets circulating in the bloodstream of said human, or to reduce the coagulant potential of said platelets, or both.

20. The method of claim 19, wherein the Antimaturation factor is intact platelet factor 4.

21. The method of claim 19, wherein the Antimaturation factor is an active peptide segment of platelet factor 4.

22. The method of claim 21, wherein the active peptide segment is a carboxy-terminal peptide segment.

23. The method of claim 22, wherein the active peptide segment contains at least about 24 amino acid residues.

24. A method for suppressing megakaryocytopoiesis in a mammal, comprising administering to the mammal a sufficient amount of Antimaturation factor to inhibit at least one of maturation of immature magakaryocyte progenitor cells and maturation of immature megakaryocyte precursor cells.

25. The method of claim 24, wherein the Antimaturation factor is intact platelet factor 4.

26. The method of claim 24, wherein the Antimaturation factor is an active corresponding peptide segment of platelet factor 4.

27. The method of claim 24, wherein the Antimaturation factor is an active homologous peptide segment of intact platelet factor 4.

* * * * *

UNITED STATES PATENT AND TRADEMARK OFFICE
CERTIFICATE OF CORRECTION

PATENT NO.   : 5,185,323
DATED        : February 9, 1993
INVENTOR(S)  : Alan M. Gewirtz It is certified that error appears in the above-identified patent and that said Letters Patent is hereby corrected as shown below:

At column 1, line 5, please insert the following:

"STATEMENT AS TO RIGHTS TO INVENTIONS MADE UNDER FEDERALLY SPONSORED RESEARCH AND DEVELOPMENT

Information contained herein was obtained through research performed under National Institute of Health Grant R01CA36896."

Signed and Sealed this

Fourth Day of July, 1995

*Attest:*

BRUCE LEHMAN

*Attesting Officer*           *Commissioner of Patents and Trademarks*